(12) United States Patent
McConnell et al.

(10) Patent No.: US 10,753,948 B2
(45) Date of Patent: Aug. 25, 2020

(54) METHOD FOR AIDING DIFFERENTIAL DIAGNOSIS OF STROKE

(71) Applicant: Randox Laboratories Ltd., Co Antrim (GB)

(72) Inventors: Ivan McConnell, County Antrim (GB); John Lamont, County Antrim (GB); Peter Fitzgerald, County Antrim (GB); Konstantinos Makris, Athens (GR)

(73) Assignee: Randox Laboratories Ltd. (GB)

( * ) Notice: Subject to any disclaimer, the term of this patent is extended or adjusted under 35 U.S.C. 154(b) by 0 days.

(21) Appl. No.: 14/895,724

(22) PCT Filed: Jun. 4, 2014

(86) PCT No.: PCT/GB2014/051721
§ 371 (c)(1),
(2) Date: Dec. 3, 2015

(87) PCT Pub. No.: WO2014/195698
PCT Pub. Date: Dec. 11, 2014

(65) Prior Publication Data
US 2016/0139147 A1    May 19, 2016

(30) Foreign Application Priority Data

Jun. 4, 2013   (GB) .................................. 1309928.8

(51) Int. Cl.
*G01N 33/68* (2006.01)

(52) U.S. Cl.
CPC . *G01N 33/6893* (2013.01); *G01N 2333/4737* (2013.01); *G01N 2333/5412* (2013.01); *G01N 2333/70503* (2013.01); *G01N 2333/70564* (2013.01); *G01N 2333/7151* (2013.01); *G01N 2800/2871* (2013.01)

(58) Field of Classification Search
None
See application file for complete search history.

(56) References Cited

U.S. PATENT DOCUMENTS

| 7,713,705 | B2 | 5/2010 | Buechler et al. |
| 2003/0199000 | A1 | 10/2003 | Valkirs et al. |
| 2004/0209307 | A1 | 10/2004 | Valkirs et al. |
| 2004/0253637 | A1 | 12/2004 | Buechler et al. |
| 2007/0005261 | A1* | 1/2007 | Serena ................ G06F 19/3443 702/19 |
| 2011/0287974 | A1* | 11/2011 | Benvenisty ........ G01N 33/5073 506/10 |

FOREIGN PATENT DOCUMENTS

| EP | 1238284 A2 | 9/2002 |
| EP | 1419388 A1 | 5/2004 |
| GB | 2497138 A | 6/2013 |
| WO | 01042793 A2 | 6/2001 |
| WO | 0212892 A2 | 2/2002 |
| WO | 03016910 A1 | 2/2003 |
| WO | 2010012834 A1 | 2/2010 |
| WO | 2010086697 A1 | 8/2010 |
| WO | 2013079981 A2 | 6/2013 |

OTHER PUBLICATIONS

International Search Report for Application No. PCT/GB2014/051721 dated Oct. 15, 2014.
William Whiteley et al: "Blood biomarkers in stroke: research and clinical practice", International Journal of Stroke, vol. 7. No. 5. Mar. 30, 2012 (Mar. 30, 2012), pp. 435-439, XP055141196.

* cited by examiner

*Primary Examiner* — Katherine D Salmon
(74) *Attorney, Agent, or Firm* — Lerner, David, Littenberg, Krumholz & Mentlik, LLP (57) ABSTRACT

The present invention provides a method of aiding the differential diagnosis of haemorrhagic stroke, ischemic stroke and a transient ischemic attack in a patient who has suffered or is suffering a stroke. The method comprises: (i) determining the concentration of the biomarkers VCAM-1, GFAP and CRP in an ex vivo sample obtained from the patient; and (ii) establishing the statistical significance of the concentration of the biomarkers. Optionally, the method further comprises steps of (iii) determining the concentration of the biomarkers IL-6 and sTNFR1 in an ex vivo sample obtained from the patient; (iv) determining the gender of the patient; and (v) establishing the statistical significance of the concentration of the five biomarkers, in conjunction with the patient's gender. The present invention also provides substrates comprising probes for VCAM-1, GFAP and CRP for use in a method for aiding the differential diagnosis of stroke.

10 Claims, 9 Drawing Sheets

METHOD FOR AIDING DIFFERENTIAL DIAGNOSIS OF STROKE

CROSS-REFERENCE TO RELATED APPLICATION

This application is a national phase entry under 35 U.S.C. § 371 of International Application No. PCT/GB2014/051721, filed Jun. 4, 2014, which claims priority to Great Britain Patent Application No. 1309928.8, filed Jun. 4, 2013, the disclosures of which are incorporated herein by reference.

BACKGROUND TO THE INVENTION

Stroke is the third leading cause of death worldwide and can be defined as the rapidly developing loss of brain function(s) due to interruption in the blood supply to the brain. According to the World Health Organisation, 15 million people per year suffer stroke worldwide, with 5 million dying and a further 5 million being permanently disabled. High blood pressure is estimated to be a contributing factor in 12.7 million of these 15 million stroke cases. In the UK, approximately 150,000 people have a stroke each year and stroke accounts for around 53,000 deaths per year. Stroke costs the economy an estimated £8 billion per year in England alone and stroke patients occupy approximately 20 percent of all acute hospital beds and 25 percent of long term beds.

Stroke can be classified into three sub-types:
  i) Ischaemic stroke (IS) occurs when blood supply to the brain is decreased, resulting in brain damage. An ischemic stroke occurs when a blood vessel becomes blocked, usually via a blood clot. This clot may form locally at an atherosclerotic plaque (thrombotic stroke) or alternatively may occur due to a travelling particle or debris that has originated from elsewhere in the bloodstream (embolic stroke);
  ii) Transient ischaemic attack (TIA) is a 'mini stroke' that occurs when blood supply to the brain is temporarily decreased. A TIA is diagnosed if symptoms are quickly resolved (within 24 hours with the individual returning to normal health); and
  iii) Haemorrhagic stroke (HS) occurs when blood accumulates within the skull vault, usually when a weakened blood vessel ruptures. Haemorrhagic stroke can be classified into two major subtypes, namely intracerebral (within the brain tissue) and subarachnoid (around the surface of the brain and under its protective layer).

IS and TIA account for approximately 85% of all stroke cases and HS accounts for 15%. In order to minimise neurological damage following stroke it is crucial that stroke patients are rapidly and accurately diagnosed, so that appropriate treatment can be administered. For example, in order to break down clots thrombolytic therapy such as tissue plasminogen activator (TPA) can be administered. However, such therapy is only warranted in IS and is detrimental in HS. The nature of TIA does not require such therapy and blood thinners such as warfarin and aspirin are prescribed in such cases.

At present, if stroke is suspected, physical symptoms are evaluated and a computerised tomography (CT) scan is usually performed. A CT scan has good sensitivity for identifying HS patients (approximately 90% sensitivity) but poor sensitivity for identifying IS and TIA patients (approximately 20% sensitivity). In practice minimal or no tissue damage occurs for TIA due to its transient nature, therefore CT scanning is ineffective as a diagnostic technique. Magnetic Resonance Imaging (MRI) has improved sensitivity for IS diagnosis (up to approximately 80%) but increased time requirements, machine accessibility, and high cost have limited its use for stroke diagnosis. The poor sensitivity of CT scanning for the detection of IS and TIA means that a biological fluid-based diagnostic biomarker tests for detecting IS and TIA would be an invaluable tool to aid clinicians in the diagnosis of stroke sub-type. Biological fluid-based biomarkers have the potential to expedite and increase the accuracy of stroke diagnosis.

Various candidate biomarkers have been proposed for the diagnosis of stroke and stroke sub-type delineation and there are several descriptions of IS/TIA versus HS discrimination in the prior art, for example EP1238284, WO 2010/086697, WO 2010/012834, and WO 2002/012892.

EP1419388 discloses data that distinguishes IS from HS and all stroke types from non-stroke controls. However, none have thus far found use in clinical practice and there is a real clinical need for biomarkers of all three stroke sub-types that have high sensitivity and specificity to enable accurate diagnosis.

Differential diagnosis between the three different stroke sub-types using a blood test would facilitate a more informed clinical decision, potentially render unnecessary expensive and less expeditious neuroimaging diagnostics, and could improve the clinical outcome for patients.

SUMMARY OF THE INVENTION

According to a first aspect, the present invention provides a method of aiding the differential diagnosis of haemorrhagic stroke, ischemic stroke and a transient ischemic attack in a patient who has suffered or is suffering a stroke, comprising: determining the concentration of the biomarkers VCAM-1, GFAP and CRP in an ex vivo sample obtained from the patient; and establishing the significance of the concentration of the biomarkers.

According to a second aspect, the present invention provides a substrate comprising probes for the biomarkers VCAM-1, GFAP and CRP for use in a method for aiding the differential diagnosis of haemorrhagic stroke, ischemic stroke and a transient ischemic attack in a patient according to the first aspect of the invention.

According to a third aspect, the invention is directed to the use of a substrate comprising probes for VCAM-1, GFAP and CRP in a method for aiding the differential diagnosis of haemorrhagic stroke, ischemic stroke and a transient ischemic attack in a patient according to the first aspect of the invention.

According to a fourth aspect, the invention is directed to the use of VCAM-1, GFAP, CRP, IL-6 and/or sTNFR1 as biomarkers of haemorrhagic stroke and/or as differentiators between haemorrhagic stroke, ischemic stroke and a transient ischaemic attack.

DETAILED DESCRIPTION OF THE INVENTION

The present invention relates to biomarker-based methods and biochips that can be used to aid discrimination between the three stroke sub-types: haemorrhagic stroke (HS), ischemic stroke (IS) and transient ischemic attack (TIA).

Unless stated otherwise, all references herein to the term 'stroke' encompasses all three forms of stroke.

As used herein, the term 'ischaemic stroke (IS)' refers to the type of stroke that occurs when blood supply to the brain is decreased, resulting in brain damage. An ischemic stroke occurs when a blood vessel becomes blocked, usually via a blood clot. This clot may form locally at an atherosclerotic plaque (thrombotic stroke) or alternatively may occur due to a travelling particle or debris that has originated from elsewhere in the bloodstream (embolic stroke). The term 'transient ischaemic attack (TIA)' refers to a 'mini stroke' that occurs when blood supply to the brain is temporarily decreased. A TIA is diagnosed if symptoms are quickly resolved (within 24 hours with the individual returning to normal health). The term 'haemorrhagic stroke (HS)' occurs when blood accumulates within the skull vault, usually when a weakened blood vessel ruptures. Haemorrhagic stroke can be classified into two major sub-types: intracerebral (within the brain tissue); and subarachnoid (around the surface of the brain and under its protective layer).

References herein to 'a patient who has suffered or is suffering a stroke' include a patient who has been diagnosed as currently suffering from a stroke or who is has been diagnosed as having previously stroke a stroke. The stroke may have been a recent event, such an event having initiated the process of the individual seeking clinical help.

The terms "subject" and "patient" may be used interchangeably herein and refer to a mammal including a non-primate (e.g. a cow, pig, horse, dog, cat, rat and mouse) and a primate (e.g. a monkey and human). Preferably the subject or patient is a human.

As used herein, the term 'biomarker' refers to a molecule present in a biological sample obtained from a patient, the concentration of which in said sample may be indicative of a pathological state. Various biomarkers that have been found by the present inventors to be useful in differentiating between different stroke sub-types, either alone or in combination with other diagnostic methods, or as complementary biomarkers in combination with other biomarkers, are described herein. A used herein, the term 'complementary biomarker' refers to a biomarker that can be used in conjunction with other stroke biomarkers to support diagnosis.

It is well understood in the art that biomarker normal or 'background' concentrations may exhibit slight variation due to, for example, age, gender or ethnic/geographical genotypes. As a result, the cut-off value used in the methods of the invention may also slightly vary due to optimization depending upon the target patient/population.

The biological sample obtained from a patient is preferably a blood, serum or plasma sample. As used herein, the term 'ex vivo' has its usual meaning in the art and refers to a sample that has been removed from a patient's body.

When a blood sample is taken from the patient for analysis, whole blood, serum or plasma is analysed. Analysis of the blood sample can be by way of several analytical methodologies such as mass spectrometry linked to a pre-separation step such as chromatography. The preferred methodology is based on immuno-detection. Immuno-detection technology is also readily incorporated into transportable or hand-held devices for use outside of the clinical environment. A quantitative immunoassay such as a Western blot or ELISA can be used to detect the amount of protein. A preferred method of analysis comprises using a multi-analyte biochip which enables several proteins to be detected and quantified simultaneously. 2D Gel Electrophoresis is also a technique that can be used for multi-analyte analysis.

A first aspect of the invention provides a method of aiding the differential diagnosis of haemorrhagic stroke (HS), ischemic stroke (IS) and a transient ischemic attack (TIA) in a patient who has suffered or is suffering a stroke, comprising: determining the concentration of VCAM-1, GFAP and CRP in an ex vivo sample obtained from the patient; and establishing the significance of the concentration of the biomarkers. Using backwards stepwise logistic regression, the present inventors have found that the biomarkers GFAP, VCAM, CRP significantly influence a prediction model that can discriminate between TIA, IS and HS.

In preferred embodiments, the method further comprises further comprises: determining the concentration of IL-6 and sTNFR1 in an ex vivo sample obtained from the patient; determining the gender of the patient; and establishing the significance of the concentration of the five biomarkers, in conjunction with the patient's gender.

Gender has been found to have a major influence on biomarker levels both in homeostasis and in disease. The present inventors have found that the five biomarkers GFAP, VCAM, CRP, IL-6 and sTNFR1, in combination with gender, can be used to develop an algorithm which can accurately predict the probability of which type of stroke the patient is presenting with to allow for the relevant treatment.

In addition to any of the embodiments described above, the method of the invention may also further comprise determining the concentration of one or of the biomarkers ICAM-1, L-selectin, P-selectin, D-dimer and FABP and using the concentration value in a statistical algorithm to distinguish between different stroke subtypes.

Preferably, each of the biomarker concentration values is inputted into a statistical algorithm or algorithms to produce an output value that correlates with a differential diagnosis of HS, IS or TIA. In one embodiment, the method is used to differentially diagnose between HS and IS/TIA.

The skilled person will be aware of numerous suitable methods for developing statistical algorithms, and all of these are within the scope of the present invention. Examples of suitable classification algorithms include multinominal logistic regression, multilayer perceptron neural network (MLP), artificial neural networks, support vector machines and random forest classifiers. The present inventors have found that both multinominal logistic regression and MPL achieve similar performance in the context of the present invention, suggesting the importance of the analytes (i.e. biomarkers) used in the methods of the invention, rather than the method used to generate the algorithmic model. However, in a preferred embodiment, the statistical algorithm includes a logistic regression equation.

The accuracy of statistical methods used in accordance with the present invention can be best described by their receiver operating characteristics (ROC). The ROC curve addresses both the sensitivity, the number of true positives, and the specificity, the number of true negatives, of the test. Therefore, sensitivity and specificity values for a given combination of biomarkers are an indication of the accuracy of the assay. For example, if a biomarker combination has sensitivity and specificity values of 80%, out of 100 patients which have stroke, 80 will be correctly identified from the determination of the presence of the particular combination of biomarkers as positive for stroke, while out of 100 patients who have not suffered a stroke 80 will accurately test negative for the disease.

If two or more biomarkers are to be used in the diagnostic method a suitable mathematical model, such as logistic regression equation, can be derived. The logistic regression equation might include other variables such as age and gender of patient. The ROC curve can be used to assess the accuracy of the logistic regression model. The logistic regression equation can be used independently or in an algorithm to aid clinical decision making. Although a logistic regression equation is a common mathematical/statistical procedure used in such cases and is preferred in the context of the present invention, other mathematical/statistical procedures can also be used.

By way of example, a logistic regression equation applicable to the present invention (at a classification cut-off value of 0.5) for the biomarker combination GFAP, CRP and VCAM for indication of stroke type in a patient suspected of having had or currently experiencing a stroke is calculated as follows:

$$\text{Probability of } IS = \frac{e^{(-3.075-0.581[GFAP]+0.094[CPR]+0.05[VCAM])}}{1 + e^{(-3.075-0.581[GFAP]+0.094[CPR]+0.05[VCAM])} + e^{(-3.605-3.979[GFAP]+0.116[CPR]+0.04[VCAM])}}$$

where [GFAP], [CRP] and [VCAM] are the concentrations of GFAP, CRP and VCAM measured in a blood sample taken from the patient (see number 118 of Table 1 for AUC value).

Preferably, the method of aiding the differential diagnosis of HS, IS and TIA is carried out on a patient who has previously been diagnosed as suffering from a stroke, or having previously suffered from a stroke. The purpose of the method of the invention is to identify which stroke sub-type the patient is suffering from, or has suffered, so that appropriate treatment can be administered. Therefore, in one embodiment, the method of the invention comprises a further step of administering appropriate treatment to the patient, once a differential diagnosis of the stroke sub-type has been made. For example, if as a result of carrying out the method of the invention it is determined that the patient has suffered, or is suffering, an IS, appropriate treatment such as thrombolytic therapy (e.g. tissue plasminogen activator (TPA)) can be administered to break-down clots. This may be administered in conjunction with other appropriate therapies, as determined by a physician. If as a result of carrying out the method of the invention it is determined that the patient has suffered, or is suffering, a TIA, blood thinners such as warfarin and aspirin may be prescribed and administered. If as a result of carrying out the method of the invention it is determined that the patient has suffered, or is suffering, a HS then these patients would typically be sent to a surgical unit to repair the damaged blood vessels.

An initial step of diagnosing the patient as suffering from, or having suffered from, a stroke may be carried out using any suitable diagnostic method or technique known in the art, including scanning techniques such as CT and MRI, or assaying a patient's sample for biomarkers of stroke. However, in a preferred embodiment, the patient has been diagnosed as suffering from, or having suffered from, a stroke by determining the concentration of at least two biomarkers in an ex vivo sample obtained from the patient and establishing the significance of the concentration of the biomarkers by comparing the concentration value for each biomarker with a corresponding control value. Preferably, the at least two biomarkers are selected from ICAM-1, L-selectin, P-selectin, VCAM-1, IL-6, sTNFR1, D-dimer and CRP, and preferably at least one of the two biomarkers is selected from ICAM-1, L-selectin, P-selectin and VCAM-1. According to this preferred method of initially diagnosing stroke, each of the patient and control biomarker concentration values is inputted into a statistical algorithm or algorithms to produce an output value that indicates whether a stroke has occurred. Preferred biomarker combinations for this embodiment of the invention are those listed in Table 1 or Table 2. These tables provide sensitivity, specificity and AUC data for different biomarker combinations for stoke v control.

TABLE 1

| Biomarker(s) | % Sensitivity | % Specificity | AUC |
| --- | --- | --- | --- |
| 1. VCAM-1 + ICAM-1 | 80.6 | 75.0 | 0.831 |
| 2. VCAM-1 + Psel | 87.8 | 71.7 | 0.913 |
| 3. VCAM-1 + Lsel | 89.8 | 86.7 | 0.943 |
| 4. VCAM-1 + IL-6 | 80.6 | 78.3 | 0.879 |
| 5. VCAM-1 + CRP | 78.6 | 75.0 | 0.826 |
| 6. VCAM-1 + D-dimer | 87.8 | 76.7 | 0.886 |
| 7. VCAM-1 + NGAL | 81.6 | 73.3 | 0.867 |
| 8. VCAM-1 + sTNFR1 | 82.7 | 75.0 | 0.832 |
| 9. IL-6 + sTNFR1 | 78.6 | 75.0 | 0.870 |
| 10. ICAM-1 + Psel | 92.9 | 76.7 | 0.932 |
| 11. ICAM-1 + Lsel | 90.8 | 90.0 | 0.954 |
| 12. ICAM-1 + IL-6 | 83.7 | 83.3 | 0.897 |
| 13. ICAM-1 + CRP | 79.6 | 80.0 | 0.822 |
| 14. ICAM-1 + D-dimer | 86.7 | 76.7 | 0.905 |
| 15. ICAM-1 + NGAL | 81.6 | 73.3 | 0.836 |
| 16. ICAM-1 + sTNFR1 | 77.6 | 73.3 | 0.832 |
| 17. IL-6 + NGAL | 87.8 | 81.7 | 0.909 |

TABLE 1-continued

| Biomarker(s) | % Sensitivity | % Specificity | AUC |
|---|---|---|---|
| 18. Psel + Lsel | 88.8 | 65.0 | 0.867 |
| 19. Psel + IL-6 | 90.8 | 78.3 | 0.937 |
| 20. Psel + CRP | 87.8 | 68.3 | 0.888 |
| 21. Psel + D-dimer | 90.8 | 85.0 | 0.931 |
| 22. Psel + NGAL | 86.7 | 58.3 | 0.838 |
| 23. Psel + sTNFR1 | 86.7 | 65.0 | 0.885 |
| 24. IL-6 + D-dimer | 84.7 | 81.7 | 0.910 |
| 25. Lsel + IL-6 | 84.7 | 85.0 | 0.907 |
| 26. Lsel + CRP | 86.7 | 71.7 | 0.863 |
| 27. Lsel + D-dimer | 88.8 | 80.0 | 0.894 |
| 28. Lsel + NGAL | 90.8 | 51.7 | 0.833 |
| 29. Lsel + sTNFR1 | 84.7 | 61.7 | 0.862 |
| 30. IL-6 + CRP | 76.5 | 81.7 | 0.870 |
| 31. IL-6 + NGAL + sTNFR1 | 89.8 | 81.7 | 0.942 |
| 32. IL-6 + D-dimer + sTFNRI | 85.7 | 80.0 | 0.908 |
| 33. IL-6 + D-dimer + NGAL | 92.9 | 83.3 | 0.943 |
| 34. IL-6 + CRP + sTNFR1 | 75.5 | 78.3 | 0.872 |
| 35. VCAM-1 + ICAM-1 + Psel | 91.8 | 80.0 | 0.946 |
| 36. VCAM-1 + ICAM-1 + Lsel | 93.9 | 93.3 | 0.975 |
| 37. VCAM-1 + ICAM-1 + IL-6 | 85.7 | 81.7 | 0.906 |
| 38. VCAM-1 + ICAM-1 + CRP | 80.6 | 78.3 | 0.853 |
| 39. VCAM-1 + ICAM-1 + D-dimer | 88.8 | 80.0 | 0.907 |
| 40. VCAM-1 + ICAM-1 + NGAL | 85.7 | 80.0 | 0.895 |
| 41. VCAM-1 + ICAM-1 + sTNFR1 | 82.7 | 75.0 | 0.856 |
| 42. IL-6 + CRP + NGAL | 85.7 | 80.0 | 0.915 |
| 43. VCAM-1 + Psel + Lsel | 92.9 | 88.3 | 0.957 |
| 44. VCAM-1 + Psel + IL-6 | 90.8 | 76.7 | 0.962 |
| 45. VCAM-1 + Psel + CRP | 87.8 | 78.3 | 0.930 |
| 46. VCAM-1 + Psel + D-dimer | 89.8 | 83.3 | 0.955 |
| 47. VCAM-1 + Psel + NGAL | 89.8 | 76.7 | 0.932 |
| 48. VCAM-1 + Psel + sTNFR1 | 88.8 | 76.7 | 0.923 |
| 49. IL-6 + CRP + D-dimer | 81.6 | 80.0 | 0.911 |
| 50. VCAM-1 + Lsel + IL-6 | 89.8 | 90.0 | 0.957 |
| 51. VCAM-1 + Lsel + CRP | 91.8 | 91.7 | 0.951 |
| 52. VCAM-1 + Lsel + D-dimer | 89.8 | 85.0 | 0.946 |
| 53. VCAM-1 + Lsel + NGAL | 92.9 | 83.3 | 0.962 |
| 54. VCAM-1 + Lsel + sTNR1 | 83.3 | 87.8 | 0.947 |
| 55. Lsel + NGAL + sTNFR1 | 89.8 | 80.0 | 0.931 |
| 56. VCAM-1 + IL-6 + CRP | 79.6 | 81.7 | 0.881 |
| 57. VCAM-1 + IL-6 + D-dimer | 86.7 | 88.3 | 0.916 |
| 58. VCAM-1 + IL-6 + NGAL | 91.8 | 86.7 | 0.941 |
| 59. VCAM-1 + IL-6 + sTNFR1 | 81.6 | 80.0 | 0.882 |
| 60. Lsel + D-dimer + sTNFR1 | 83.7 | 76.7 | 0.905 |
| 61. VCAM-1 + CRP + D-dimer | 85.7 | 81.7 | 0.895 |
| 62. VCAM-1 + CRP + NGAL | 87.8 | 81.7 | 0.911 |
| 63. VCAM-1 + CRP + sTNFR1 | 80.6 | 78.3 | 0.837 |
| 64. Lsel + D-dimer + NGAL | 91.8 | 85.0 | 0.921 |
| 65. VCAM-1 + D-dimer + NGAL | 90.8 | 96.7 | 0.938 |
| 66. VCAM-1 + D-dimer + sTNFR1 | 87.8 | 80.0 | 0.891 |
| 67. Lsel + CRP + sTNFR1 | 84.7 | 73.3 | 0.875 |
| 68. VCAM-1 + NGAL + sTNFR1 | 89.8 | 80.0 | 0.930 |
| 69. Lsel + CRP + D-dimer | 86.7 | 76.7 | 0.908 |
| 70. Lsel + CRP + NGAL | 86.7 | 73.3 | 0.882 |
| 71. ICAM-1 + Psel + Lsel | 95.9 | 91.7 | 0.977 |
| 72. ICAM-1 + Psel + IL-6 | 93.9 | 91.7 | 0.979 |
| 73. ICAM-1 + Psel + CRP | 92.9 | 83.3 | 0.949 |
| 74. ICAM-1 + Psel + D-dimer | 93.9 | 88.3 | 0.969 |
| 75. ICAM-1 + Psel + NGAL | 88.8 | 78.3 | 0.938 |
| 76. ICAM-1 + Psel + sTNFR1 | 91.8 | 81.7 | 0.946 |
| 77. Lsel + IL-6 + sTNFR1 | 84.7 | 81.7 | 0.911 |
| 78. ICAM-1 + Lsel + IL-6 | 92.9 | 90.0 | 0.975 |
| 79. ICAM-1 + Lsel + CRP | 89.8 | 90.0 | 0.958 |
| 80. ICAM-1 + Lsel + D-dimer | 90.8 | 88.3 | 0.964 |
| 81. ICAM-1 + Lsel + NGAL | 91.8 | 86.7 | 0.963 |
| 82. ICAM-1 + Lsel + sTNFR1 | 91.8 | 88.3 | 0.965 |
| 83. Lsel + IL-6 + NGAL | 90.8 | 83.3 | 0.920 |
| 84. ICAM-1 + IL-6 + CRP | 83.7 | 83.3 | 0.896 |
| 85. ICAM-1 + IL-6 + D-dimer | 87.8 | 85.0 | 0.931 |
| 86. ICAM-1 + IL-6 + NGAL | 89.8 | 86.7 | 0.934 |
| 87. ICAM-1 + IL-6 + sTNFR1 | 84.7 | 80.0 | 0.903 |
| 88. Lsel + IL-6 + D-dimer | 86.7 | 81.7 | 0.920 |
| 89. ICAM-1 + CRP + D-dimer | 88.0 | 85.0 | 0.911 |
| 90. ICAM-1 + CRP + NGAL | 85.7 | 76.7 | 0.882 |
| 91. ICAM-1 + CRP + sTNFR1 | 77.6 | 73.3 | 0.844 |
| 92. Lsel + IL-6 + CRP | 87.8 | 81.7 | 0.914 |
| 93. ICAM-1 + D-dimer + NGAL | 90.8 | 83.3 | 0.932 |
| 94. ICAM-1 + D-dimer + sTNFR1 | 87.8 | 80.0 | 0.909 |
| 95. Psel + NGAL + sTNFR1 | 89.8 | 76.7 | 0.930 |

TABLE 1-continued

| Biomarker(s) | % Sensitivity | % Specificity | AUC |
|---|---|---|---|
| 97. ICAM-1 + NGAL + sTNFR1 | 87.8 | 83.3 | 0.920 |
| 98. Psel + D-dimer + sTNFR1 | 89.8 | 81.7 | 0.930 |
| 99. Psel + D-dimer + NGAL | 91.8 | 86.7 | 0.947 |
| 100. Psel + Lsel + IL-6 | 89.8 | 78.3 | 0.943 |
| 101. Psel + Lsel + CRP | 89.8 | 75.0 | 0.903 |
| 102. Psel + Lsel + D-dimer | 90.8 | 83.3 | 0.936 |
| 103. Psel + Lsel + NGAL | 88.8 | 70.0 | 0.873 |
| 104. Psel + Lsel + sTNFR1 | 90.8 | 71.7 | 0.914 |
| 105. Psel + CRP + sTNFR1 | 87.8 | 70.0 | 0.897 |
| 106. Psel + IL-6 + CRP | 88.8 | 76.7 | 0.945 |
| 107. Psel + IL-6 + D-dimer | 90.8 | 88.3 | 0.957 |
| 108. Psel + IL-6 + NGAL | 92.9 | 88.3 | 0.953 |
| 109. Psel + IL-6 + sTNDRI | 89.8 | 78.3 | 0.944 |
| 110. Psel + CRP + NGAL | 86.7 | 75.0 | 0.907 |
| 111. Psel + CRP + D-dimer | 91.8 | 85.0 | 0.946 |
| 112. VCAM-1 + IL-6 + NGAL + sTNFR1 | 91.8 | 90.0 | 0.961 |
| 113. VCAM-1 + D-dimer + NGAL + sTNFR1 | 89.8 | 88.3 | 0.959 |
| 114. ICAM-1 + Lsel + IL-6 + D-dimer | 92.9 | 90.0 | 0.980 |
| 115. ICAM-1 + Lsel + IL-6 + NGAL | 94.9 | 91.7 | 0.983 |
| 116. ICAM-1 + Lsel + IL-6 + sTNFR1 | 92.9 | 91.7 | 0.978 |
| 117. ICAM-1 + Lsel + D-dimer + NGAL | 94.9 | 91.7 | 0.975 |
| 118. ICAM-1 + Lsel + D-dimer + sTNFR1 | 93.9 | 90.0 | 0.975 |
| 119. ICAM-1 + Lsel + NGAL + sTNFR1 | 96.9 | 95.0 | 0.978 |
| 120. ICAM-1 + IL-6 + D-dimer + NGAL | 91.8 | 88.3 | 0.966 |
| 121. ICAM-1 + IL-6 + D-dimer + sTNFR1 | 86.7 | 86.7 | 0.932 |
| 122. ICAM-1 + IL-6 + NGAL + sTNFR1 | 92.9 | 85.0 | 0.967 |
| 123. ICAM-1 + D-dimer + NGAL + sTNFR1 | 91.8 | 85.0 | 0.959 |
| 124. Lsel + IL-6 + D-dimer + NGAL | 92.9 | 88.3 | 0.948 |
| 125. Psel + Lsel + IL-6 + ICAM-1 | 95.9 | 95.0 | 0.995 |
| 126. Lsel + IL-6 + NGAL + sTNFR1 | 93.9 | 85.0 | 0.958 |
| 127. Lsel + D-dimer + NGAL + sTNFR1 | 90.8 | 86.7 | 0.946 |
| 128. VCAM-1 + ICAM-1 + Lsel + IL-6 | 96.9 | 95.0 | 0.985 |
| 129. VCAM-1 + ICAM-1 + Lsel + D-dimer | 94.9 | 93.3 | 0.978 |
| 130. VCAM-1 + ICAM-1 + Lsel + NGAL | 96.9 | 93.3 | 0.984 |
| 131. VCAM-1 + ICAM-1 + Lsel + sTNFR1 | 94.9 | 95.0 | 0.977 |
| 132. VCAM-1 + ICAM-1 + IL-6 + D-dimer | 86.7 | 86.7 | 0.933 |
| 133. VCAM-1 + ICAM-1 + IL-6 + NGAL | 91.8 | 83.3 | 0.954 |
| 134. Psel + Lsel + IL-6 + VCAM-1 | 93.9 | 86.7 | 0.972 |
| 135. VCAM-1 + ICAM-1 + D-dimer + NGAL | 89.8 | 80.0 | 0.948 |
| 136. Psel + Lsel + IL-6 + D-dimer | 89.8 | 88.3 | 0.959 |
| 137. VCAM-1 + ICAM-1 + NGAL + sTNRI | 85.7 | 81.7 | 0.944 |
| 138. VCAM-1 + Lsel + IL-6 + D-dimer | 90.8 | 91.7 | 0.956 |
| 139. VCAM-1 + Lsel + IL-6 + NGAL | 92.9 | 91.7 | 0.972 |
| 140. VCAM-1 + Lsel + IL-6 + sTNFR1 | 88.8 | 90.0 | 0.959 |
| 141. VCAM-1 + Lsel + D-dimer + NGAL | 93.9 | 90.0 | 0.968 |
| 142. VCAM-1 + Lsel + D-dimer + sTNFR1 | 92.9 | 88.3 | 0.949 |
| 143. VCAM-1 + Lsel + NGAL + sTNFR1 | 91.8 | 90.0 | 0.970 |
| 144. VCAM-1 + IL-6 + D-dimer + NGAL | 92.9 | 88.3 | 0.971 |
| 145. IL-6 + D-dimer + NGAL + sTNFR1 | 89.8 | 88.3 | 0.971 |
| 146. Psel + Lsel + IL-6 + NGAL | 93.9 | 85.0 | 0.953 |
| 147. CRP + D-dimer + ICAM-1 + IL-6 | 87.8 | 85.0 | 0.932 |
| 148. CRP + D-dimer + ICAM-1 + Lsel | 91.8 | 91.7 | 0.966 |
| 149. CRP + D-dimer + ICAM-1 + NGAL | 87.8 | 83.3 | 0.939 |
| 150. Psel + Lsel + ICAM-1 + D-dimer | 98.0 | 93.3 | 0.989 |
| 151. Psel + Lsel + ICAM-1 + CRP | 95.9 | 90.0 | 0.980 |
| 152. Psel + IL-6 + ICAM-1 + D-dimer | 95.9 | 93.3 | 0.988 |
| 153. CRP + D-dimer + IL-6 + NGAL | 91.8 | 85.0 | 0.948 |
| 154. CRP + Lsel + sTNFR1 + VCAM-1 | 87.8 | 90.0 | 0.952 |
| 155. Psel + IL-6 + ICAM-1 + NGAL | 94.9 | 90.0 | 0.983 |
| 156. CRP + D-dimer + Lsel + NGAL | 93.9 | 80.0 | 0.935 |
| 157. CRP + Lsel + NGAL + sTNFR1 | 91.8 | 81.7 | 0.933 |
| 158. CRP + D-dimer + Lsel + VCAM-1 | 88.3 | 91.8 | 0.950 |
| 159. Lsel + Psel + VCAM-1 + ICAM-1 | 94.9 | 95.0 | 0.986 |
| 160. CRP + D-dimer + NGAL + VCAM-1 | 90.8 | 85.0 | 0.950 |
| 161. CRP + IL-6 + NGAL + VCAM-1 | 90.8 | 88.3 | 0.947 |
| 162. CRP + ICAM-1 + IL-6 + Lsel | 92.9 | 90.0 | 0.975 |
| 163. CRP + ICAM-1 + IL-6 + NGAL | 88.8 | 83.3 | 0.938 |
| 164. CRP + IL-6 + NGAL + sTNFR1 | 89.8 | 80.0 | 0.947 |
| 165. CRP + IL-6 + Lsel + VCAM-1 | 90.8 | 91.7 | 0.957 |
| 166. CRP + ICAM-1 + Lsel + NGAL | 94.9 | 88.3 | 0.970 |
| 167. CRP + ICAM-1 + Lsel + sTNFR1 | 91.8 | 88.3 | 0.968 |
| 168. CRP + ICAM-1 + Lsel + VCAM-1 | 93.9 | 95.0 | 0.976 |

TABLE 1-continued

| Biomarker(s) | % Sensitivity | % Specificity | AUC |
|---|---|---|---|
| 169. CRP + IL-6 + Lsel + NGAL | 88.8 | 83.3 | 0.931 |
| 170. CRP + NGAL + sTNFR1 + VCAM-1 | 87.8 | 85.0 | 0.934 |

[Lsel (L-selectin) Psel (P-selectin)]

TABLE 2

| Biomarkers | % Sensitivity | % Specificity | AUC |
|---|---|---|---|
| 1. VCAM1 + FABP | 89.8 | 95.0 | 0.960 |
| 2. ICAM1 + FABP | 92.9 | 93.3 | 0.964 |
| 3. Psel + FABP | 95.9 | 91.7 | 0.981 |
| 4. Lsel + FABP | 91.8 | 95.0 | 0.970 |
| 5. VCAM1 + ICAM1 + FABP | 92.9 | 93.3 | 0.965 |
| 6. VCAM1 + Psel + FABP | 95.9 | 91.7 | 0.983 |
| 7. VCAM1 + Lsel + FABP | 92.9 | 96.7 | 0.971 |
| 8. VCAM1 + IL6 + FABP | 90.8 | 95.0 | 0.961 |
| 9. VCAM1 + CRP + FABP | 89.8 | 95.0 | 0.960 |
| 10. VCAM1 + D-dimer + FABP | 90.8 | 95.0 | 0.963 |
| 11. VCAM1 + NGAL + FABP | 98.0 | 93.3 | 0.986 |
| 12. VCAM1 + sTNFR1 + FABP | 89.8 | 91.7 | 0.962 |
| 13. ICAM1 + Psel + FABP | 96.9 | 93.3 | 0.990 |
| 14. ICAM1 + Lsel + FABP | 96.9 | 93.3 | 0.993 |
| 15. ICAM1 + IL6 + FABP | 91.8 | 91.7 | 0.966 |
| 16. ICAM1 + CRP + FABP | 92.9 | 93.3 | 0.964 |
| 17. ICAM1 + D-dimer + FABP | 92.9 | 95.0 | 0.968 |
| 18. ICAM1 + NGAL + FABP | 96.9 | 95.0 | 0.984 |
| 19. ICAM1 + sTNFR1 + FABP | 91.8 | 93.3 | 0.966 |
| 20. Psel + Lsel + FABP | 95.9 | 93.3 | 0.985 |
| 21. Psel + IL6 + FABP | 93.9 | 93.3 | 0.985 |
| 22. Psel + CRP + FABP | 92.9 | 91.7 | 0.983 |
| 23. Psel + D-dimer + FABP | 93.9 | 93.3 | 0.984 |
| 24. Psel + NGAL + FABP | 96.9 | 96.7 | 0.993 |
| 25. Psel + sTNFR1 + FABP | 93.9 | 91.7 | 0.983 |
| 26. Lsel + IL6 + FABP | 90.8 | 93.3 | 0.975 |
| 27. Lsel + CRP + FABP | 91.8 | 93.3 | 0.970 |
| 28. IL6 + CRP + FABP | 91.8 | 96.7 | 0.962 |
| 29. IL6 + D-dimer + FABP | 89.8 | 93.3 | 0.963 |
| 30. IL6 + NGAL + FABP | 91.8 | 93.3 | 0.990 |
| 31. IL6 + sTNFR1 + FABP | 89.8 | 91.7 | 0.963 |
| 32. Lsel + D-dimer + FABP | 90.8 | 93.3 | 0.973 |
| 33. Lsel + NGAL + FABP | 95.9 | 93.3 | 0.989 |
| 34. Lsel + sTNFR1 + FABP | 92.9 | 93.3 | 0.972 |
| 35. FABP + CRP + D-dimer | 90.8 | 93.3 | 0.962 |
| 36. FABP + CRP + NGAL | 95.9 | 93.3 | 0.985 |
| 37. FABP + CRP + sTNFR1 | 90.8 | 93.3 | 0.959 |
| 38. FABP + D-dimer + NGAL | 95.9 | 93.3 | 0.985 |
| 39. FABP + D-dimer + sTNFR1 | 91.8 | 93.3 | 0.962 |
| 40. CRP + IL6 + FABP | 89.8 | 93.3 | 0.962 |
| 41. D-dimer + IL6 + FABP | 91.8 | 93.3 | 0.963 |
| 42. NGAL + IL6 + FABP | 95.9 | 93.3 | 0.990 |
| 43. sTNFR1 + IL6 + FABP | 89.8 | 91.7 | 0.963 |
| 44. IL6 + NGAL + FABP + D-dimer | 96.9 | 93.3 | 0.990 |
| 45. Lsel + NGAL + FABP + D-dimer | 95.9 | 93.3 | 0.992 |
| 46. Lsel + NGAL + FABP + IL6 | 94.9 | 93.3 | 0.994 |
| 47. Psel + sTNFR1 + FABP + D-dimer | 93.9 | 93.3 | 0.985 |
| 48. Psel + sTNFR1 + FABP + NGAL | 96.9 | 96.7 | 0.994 |
| 49. Psel + IL6 + FABP + D-dimer | 93.9 | 91.7 | 0.986 |
| 50. Psel + IL6 + FABP + NGAL | 96.9 | 95.0 | 0.996 |
| 51. Psel + Lsel + FABP + D-dimer | 95.9 | 93.3 | 0.987 |
| 52. Psel + Lsel + FABP + IL6 | 93.9 | 91.7 | 0.987 |
| 53. Psel + Lsel + FABP + NGAL | 96.9 | 96.7 | 0.994 |
| 54. Psel + Lsel + FABP + CRP | 94.9 | 93.3 | 0.985 |
| 55. ICAM1 + NGAL + FABP + IL6 | 95.9 | 93.3 | 0.991 |
| 56. ICAM1 + NGAL + FABP + D-dimer | 96.9 | 95.0 | 0.986 |
| 57. ICAM1 + NGAL + FABP + CRP | 96.9 | 95.0 | 0.986 |
| 58. ICAM1 + Lsel + FABP + IL6 | 95.9 | 95.0 | 0.994 |
| 59. ICAM1 + Lsel + FABP + NGAL | 99.0 | 96.7 | 0.996 |
| 60. ICAM1 + Lsel + FABP + D-dimer | 96.9 | 95.0 | 0.993 |
| 61. ICAM1 + Lsel + FABP + CRP | 96.9 | 93.3 | 0.993 |
| 62. ICAM1 + Lsel + FABP + sTNFR1 | 96.9 | 93.3 | 0.993 |
| 63. ICAM1 + Psel + FABP + IL6 | 98.0 | 95.0 | 0.994 |
| 64. ICAM1 + Psel + FABP + NGAL | 96.9 | 96.7 | 0.996 |
| 65. ICAM1 + Psel + FABP + D-dimer | 96.9 | 93.3 | 0.991 |
| 66. ICAM1 + Psel + FABP + CRP | 98.0 | 91.7 | 0.990 |
| 67. ICAM1 + Psel + FABP + sTNFR1 | 96.9 | 93.3 | 0.990 |

TABLE 2-continued

| Biomarkers | % Sensitivity | % Specificity | AUC |
|---|---|---|---|
| 68. ICAM1 + Psel + Lsel + FABP | 100.0 | 95.0 | 0.997 |
| 69. VCAM1 + NGAL + FABP + D-dimer | 96.9 | 93.3 | 0.988 |
| 70. VCAM1 + ICAM1 + Lsel + FABP | 99.0 | 95.0 | 0.993 |
| 71. VCAM1 + Lsel + FABP + D-dimer | 92.9 | 95.0 | 0.971 |
| 72. VCAM1 + Lsel + FABP + NGAL | 96.9 | 93.3 | 0.991 |
| 73. FABP + NGAL + sTNFR1 | 95.9 | 93.3 | 0.986 |

[Lsel (L-selectin) Psel (P-selectin)]

In the preferred method of initially diagnosing stroke described above control values can be derived from the concentration of corresponding biomarkers in a biological sample obtained from an individual or individuals who have not undergone a stroke. Such individual(s) who have not undergone stroke may be, for example, healthy individuals, individuals suffering from diseases other than stroke. Alternatively, the control values may correspond to the concentration of each of the biomarker in a sample obtained from the patient prior to the stroke event.

For the avoidance of doubt, the term 'corresponding biomarkers' means that concentrations of the same combination of biomarkers that are determined in respect of the patient's sample are also used to determine the control values. For example, if the concentration of ICAM-1 and L-selectin in the patient's sample is determined, then the concentration of ICAM-1 and L-selectin in the control sample will also be determined.

In a preferred embodiment, each of the patient and/or control biomarker concentration values is inputted into one or more statistical algorithms to produce an output value that indicates whether a stroke has occurred.

The cut-off concentrations or values are derived using a statistical technique; various different methods are available for developing statistical algorithms and are well-known to those skilled in the art. A standard method of biomarker statistical analysis is to use univariate methods to compare biomarker levels in various groups and highlight those biomarkers whose concentrations significantly differ across and between particular groups.

Biomarker concentrations can be determined by contacting the sample with a substrate having probes specific for each of the biomarkers included in the combination of biomarkers. Interactions between a biomarker and its respective probe can be monitored and quantified using various techniques that are well-known in the art. Biomarker concentrations are preferably measured in ng/ml.

Accordingly, a second aspect of the present invention provides a substrate comprising probes specific for VCAM-1, GFAP and CRP. The substrate is suitable for use in the method of the invention for aiding the differential diagnosis of HS, IS and TIA. Preferably, the substrate further comprises probes specific for IL-6 and sTNFR1, and may optionally further comprise probes for any one or more of the biomarkers listed in Tables 1 and/or 2.

As used herein, the term 'specific' means that the probe binds only to one of the biomarkers of the invention, with negligible binding to other biomarkers of the invention or to other analytes in the biological sample being analysed. This ensures that the integrity of the diagnostic assay and its result using the biomarkers of the invention is not compromised by additional binding events.

Preferably the probes are immobilised on the surface of the substrate, preferably covalently immobilised. The substrate can be any substance able to support one or more probes, but is preferably a solid state device, such as a biochip. A biochip is a planar substrate that may be, for example, mineral or polymer based, but is preferably ceramic. When identifying the various biomarkers/proteins of the invention it will be apparent to the skilled person that as well as identifying the full length protein, the identification of a fragment or several fragments of a protein is possible, provided this allows accurate identification of the protein. Similarly, although a preferred probe of the invention is a polyclonal or monoclonal antibody, other probes such as aptamers, molecular imprinted polymers, phages, short chain antibody fragments and other antibody-based probes may be used.

Preferably, a solid state device is used in the methods of the present invention, preferably the Biochip Array Technology system (BAT) (available from Randox Laboratories Limited). More preferably, the Evidence Evolution and Evidence Investigator apparatus (available from Randox Laboratories) may be used to determine the levels of biomarkers in the sample.

In a related third aspect of the invention, a substrate comprising probes for VCAM-1, GFAP and CRP according to the second aspect of the invention is used in a method for aiding the differential diagnosis of haemorrhagic stroke, ischemic stroke and a transient ischemic attack in a patient according to the first aspect of the invention.

According to a fourth aspect, the invention is directed to the use of VCAM-1, GFAP, CRP, IL-6 and/or sTNFR1 as biomarkers of haemorrhagic stroke and/or as differentiators between haemorrhagic stroke, ischemic stroke and a transient ischaemic attack.

The present invention also provides kits comprising probes for VCAM-1, GFAP and CRP, and optionally also IL-6 and/or sTNFR1, additional reagents, substrate/reaction surfaces and/or instructions for use. Such kits can be used to differentially diagnose stroke sub-types in a patient according to the first aspect of the invention.

The invention will now be described further by reference to the following non-limiting example.

Example

Patient Group

The study consisted of 98 patients displaying stroke symptoms admitted to the Emergency Department of KAT General Hospital, Athens, Greece. Blood samples were taken at the time of admission and at days 1, 2, 3 and 7. The mean time from the onset of stroke symptoms and hospital admission was 3.2 hours. The mean age of the patients was 75.2 years (standard deviation 9.4). Clinician evaluation (using criteria highlighted in the Background section) and neuroimaging techniques identified 44 ischaemic stroke (IS), 25 haemorrhagic stroke (HS), 29 transient ischemic attack (TIA); 60 healthy subjects served as controls (C).

Sample Analysis

The following proteins were tested against EDTA plasma samples of blood obtained from the patients of the study group: VCAM-1, GFAP, CRP, IL-6 and sTNFR1. The proteins were detected and quantified using multiplexed biochips incorporating biomarker-specific antibodies and the Evidence Investigator (Randox Laboratories Ltd, Crumlin, UK). The simultaneous immunoassays were performed according to manufacturer's instructions. A nine-point calibration curve and three reference controls were assayed for each biomarker to allow validation of results. For CRP IS vs TIA analysis, samples were diluted tenfold.

Figure 1:
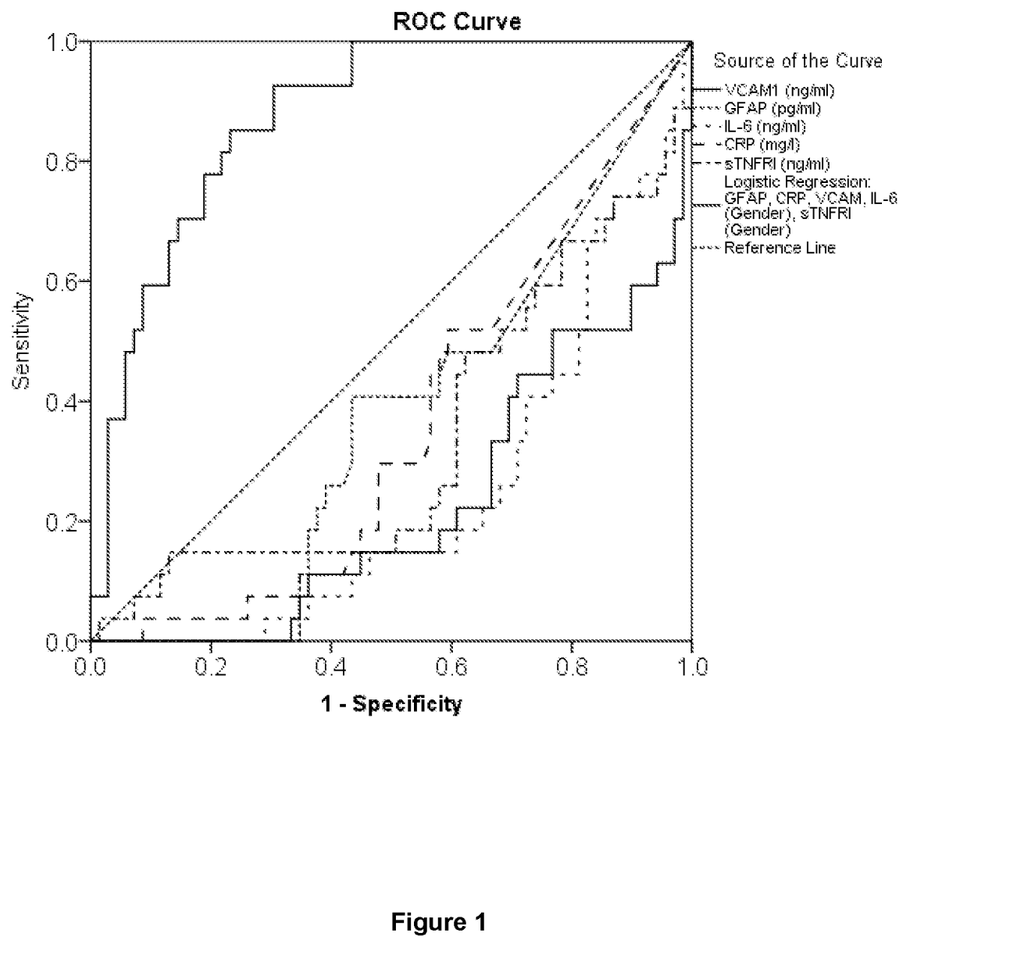
FIG. 1 is a ROC curve analysis for distinguishing TIA from other stroke types using the biomarkers of the invention.
Figure 2:
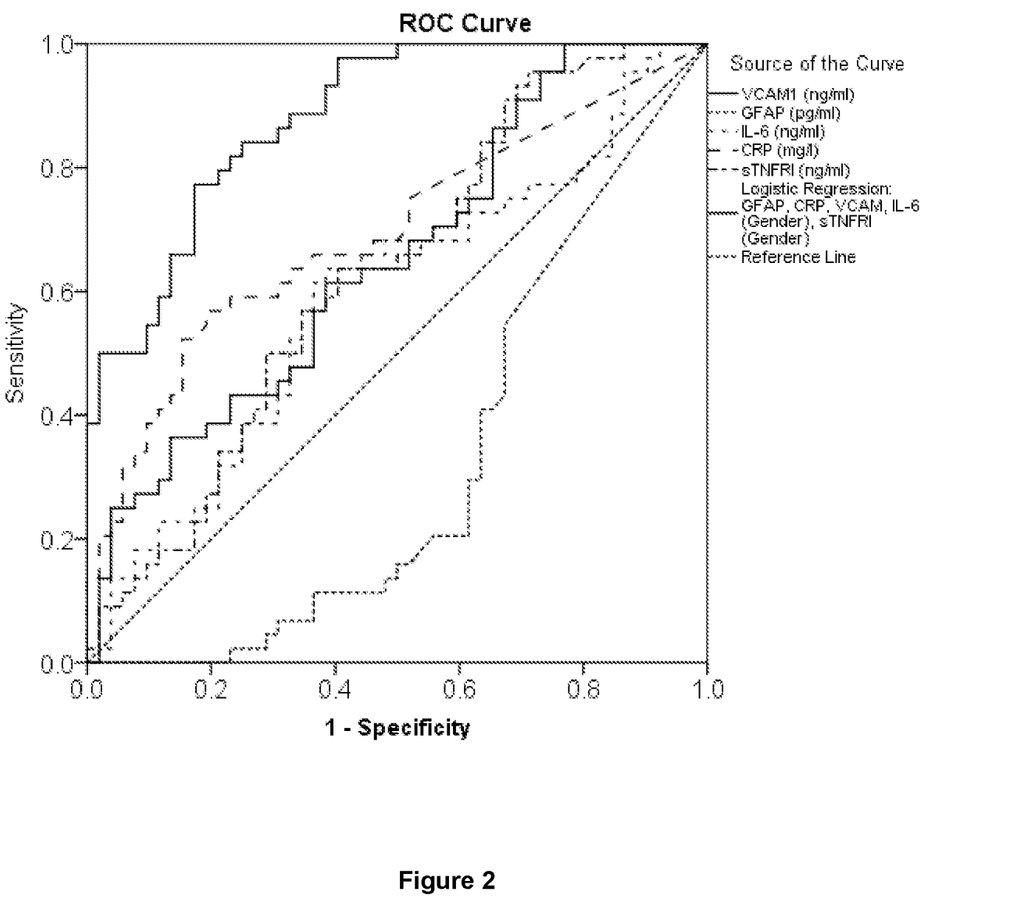
FIG. 2 is a ROC curve analysis for distinguishing IS from other stroke types using the biomarkers of the invention.
Figure 3:
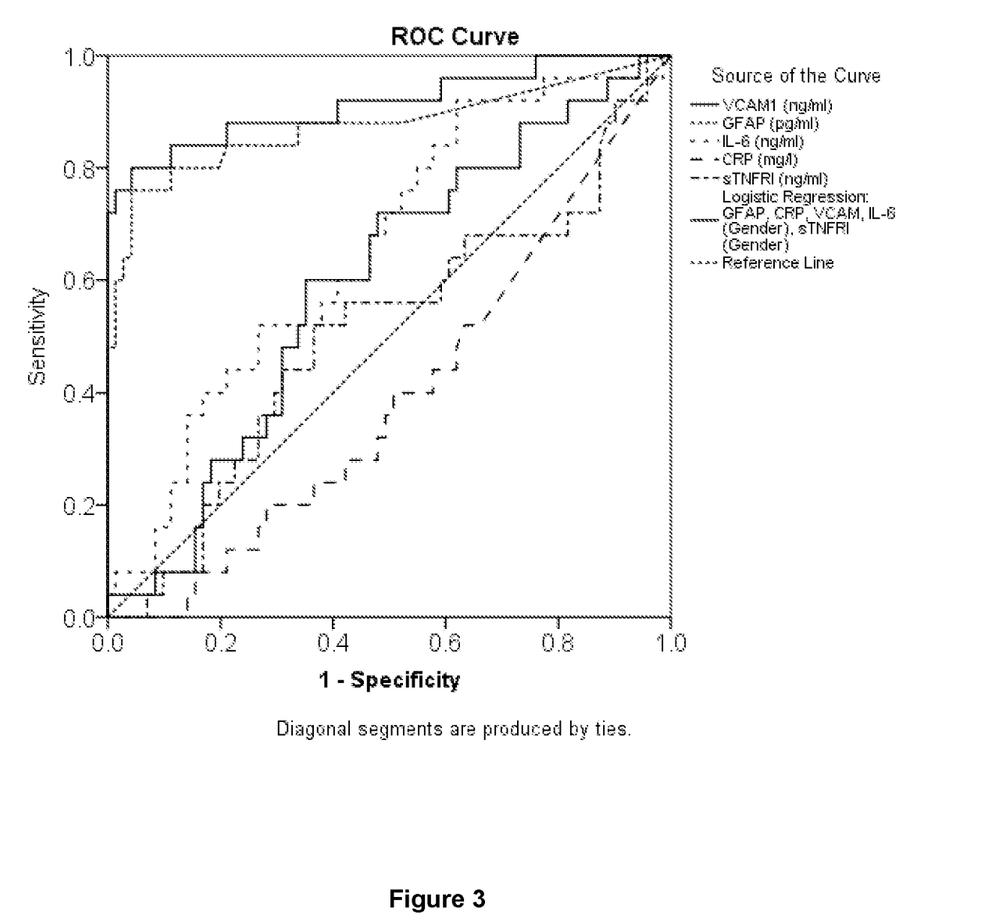
FIG. 3 is a ROC curve analysis for distinguishing HS from other stroke types using the biomarkers of the invention.
Figure 4:
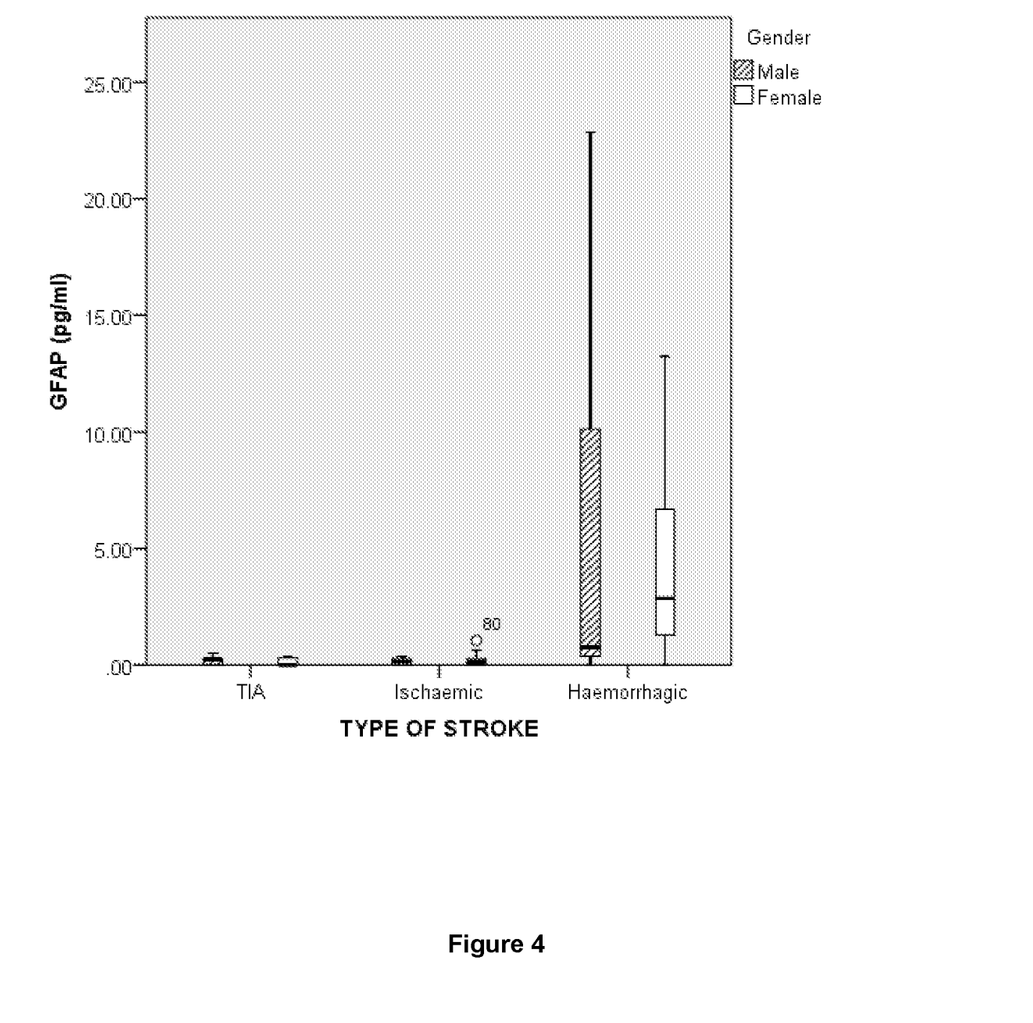
FIG. 4 is a graph showing the concentration of GFAP for each stroke sub-type in both male and female subjects.
Figure 5:
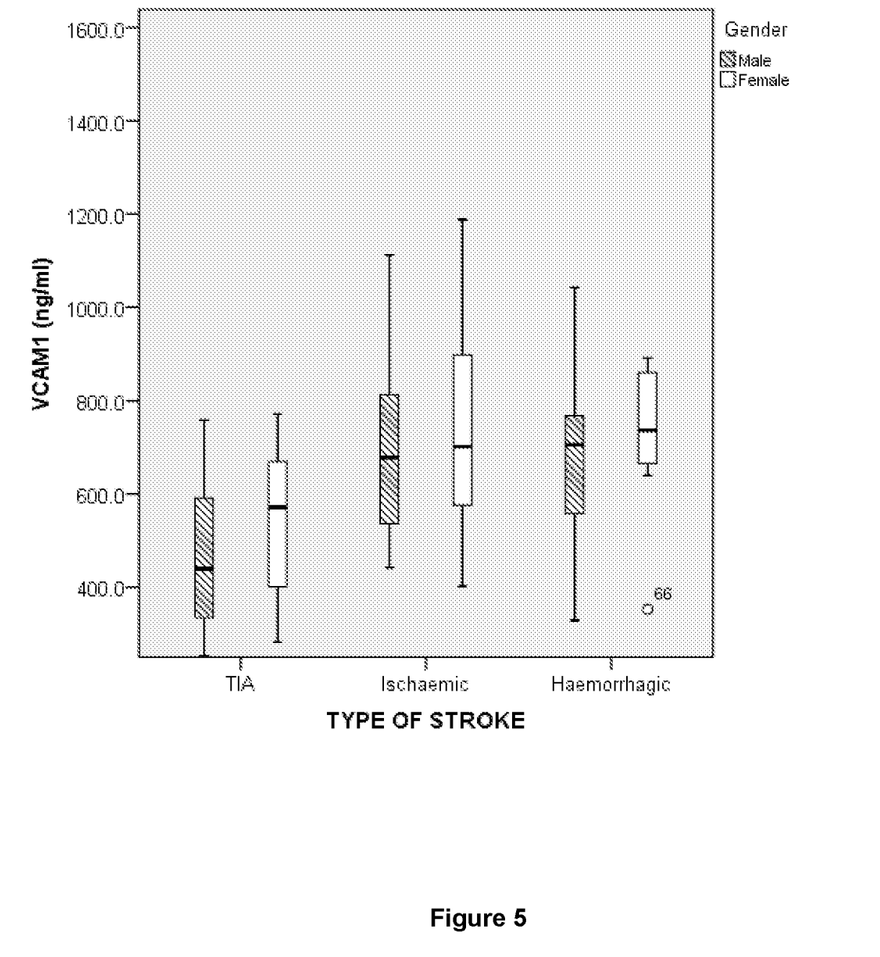
FIG. 5 is a graph showing the concentration of VCAM1 for each stroke sub-type in both male and female subjects.
Figure 6:
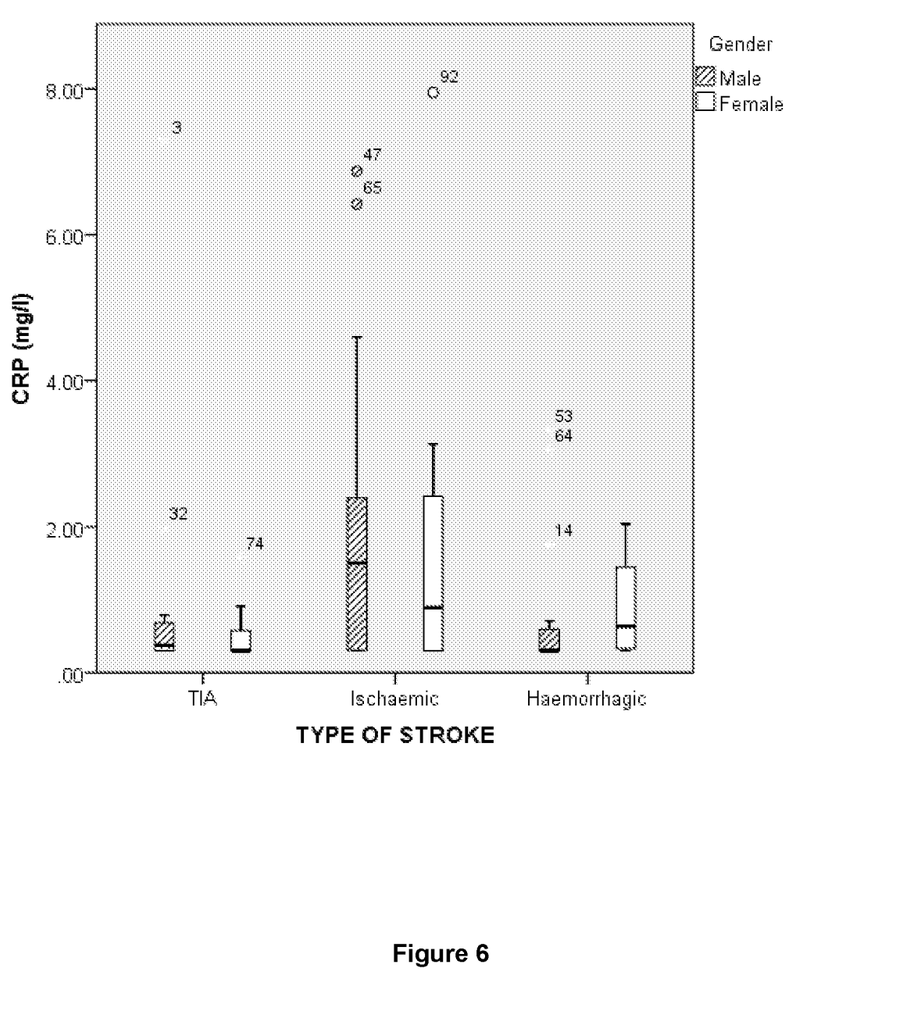
FIG. 6 is a graph showing the concentration of CRP for each stroke sub-type in both male and female subjects.
Figure 7:
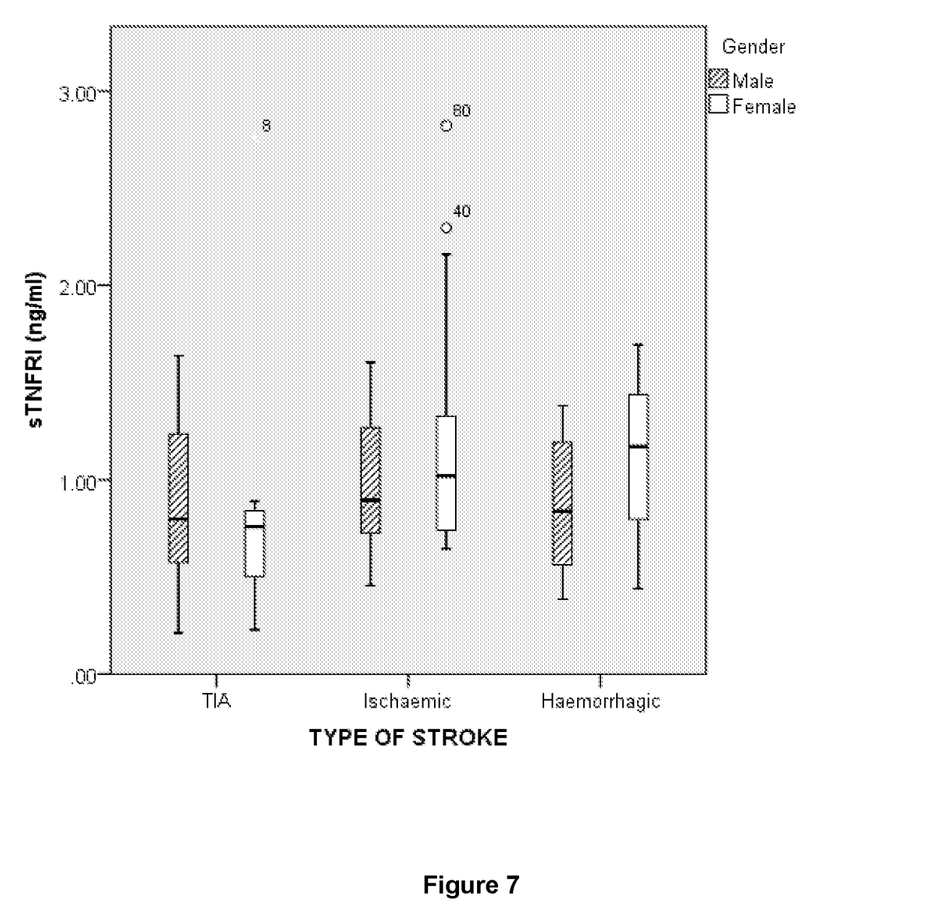
FIG. 7 is a graph showing the concentration of sTNFR1 for each stroke sub-type in both male and female subjects.
Figure 8:
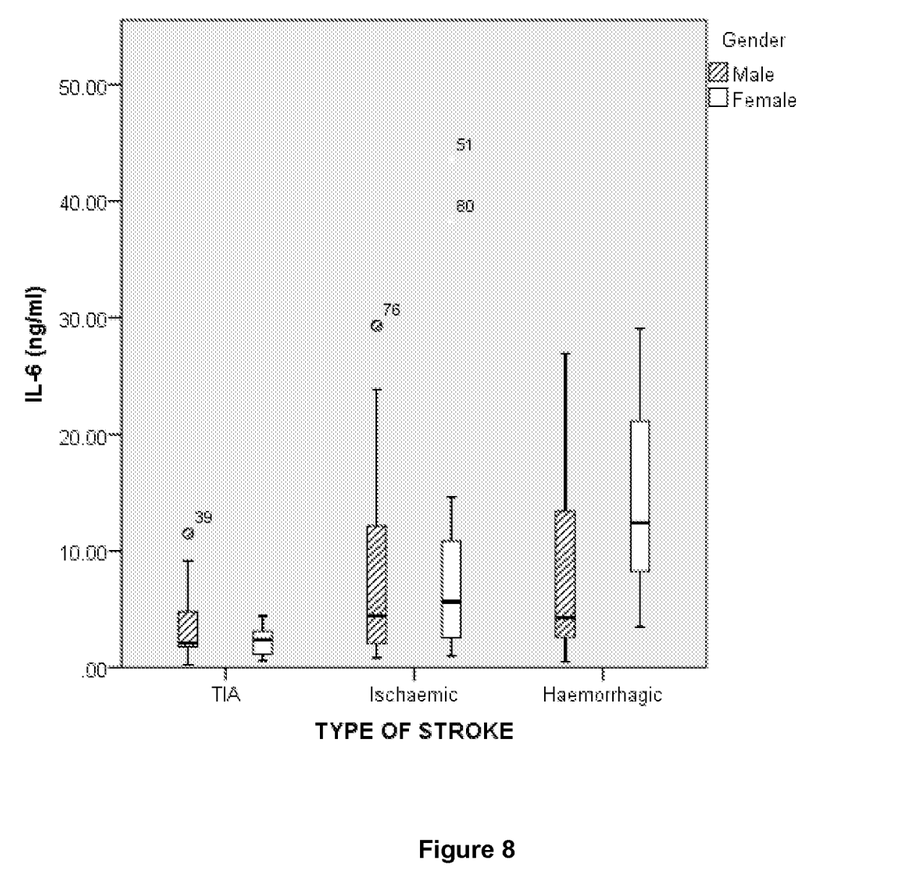
FIG. 8 is a graph showing the concentration of IL-6 for each stroke sub-type in both male and female subjects.

Statistical Analysis Single biomarkers were subject to ROC curve analysis to assess sensitivity and specificity. Logistic regression was used to model the dependency of stroke and stroke subtype upon the concentration of various combinations of biomarkers followed by ROC curve analysis to assess the model's classification accuracy. The results are shown in FIGS. 1-3.

The relevance of gender on each of the biomarkers for determining stroke subtype is shown in FIGS. 4-8.

Results

The data shown in Table 3 show the use of the biomarkers of the invention to distinguish HS from IS/TIA. The ROC curve analysis for distinguishing HS from IS and TIA patients using the biomarkers of the invention is shown in FIG. 3.

TABLE 3

| Biomarker(s) | Haemorrhagic Stroke (HS) | | |
|---|---|---|---|
| | AUC | % Sensitivity | % Specificity |
| GFAP | 0.872 | 48 | 100 |
| GFAP, IL-6 and VCAM-1 | 0.886 | 60 | 100 |
| GFAP, CRP and VCAM-1 | 0.901 | 60 | 100 |
| GFAP, CRP, VCAM-1, IL-6 (gender) sTNFR1 (gender) | 0.914 | 72 | 100 |

Furthermore, FIGS. 1-3 and Table 4 illustrate that the use of a combination of the biomarkers to categorise all stroke patients as either TIA, IS or HS patients, in this instance using multinominal logistic regression, gives an improved discrimination over any of the biomarkers in isolation.

TABLE 4

| Variable | TIA | | | | IS | | | | HS | | | |
|---|---|---|---|---|---|---|---|---|---|---|---|---|
| | AUC | S.E. | P-value | 95% CI | AUC | S.E. | P-value | 95% CI | AUC | S.E. | P-value | 95% CI |
| VCAM1 (ng/ml) | 0.224 | 0.051 | 0.000 | 0.125 0.324 | 0.652 | 0.056 | 0.011 | 0.543 0.761 | 0.594 | 0.064 | 0.165 | 0.469 0.718 |
| GFAP (pg/ml) | 0.367 | 0.059 | 0.043 | 0.252 0.481 | 0.318 | 0.055 | 0.002 | 0.211 0.425 | 0.875 | 0.052 | 0.000 | 0.774 0.976 |
| IL-6 (ng/ml) | 0.239 | 0.05 | 0.000 | 0.141 0.338 | 0.591 | 0.059 | 0.124 | 0.476 0.707 | 0.656 | 0.062 | 0.021 | 0.535 0.776 |
| CRP (mg/l) | 0.36 | 0.058 | 0.034 | 0.246 0.475 | 0.695 | 0.055 | 0.001 | 0.587 0.803 | 0.395 | 0.063 | 0.119 | 0.271 0.519 |
| sTNFR1 (ng/ml) | 0.336 | 0.064 | 0.013 | 0.211 0.461 | 0.629 | 0.057 | 0.030 | 0.518 0.74 | 0.506 | 0.07 | 0.933 | 0.368 0.643 |
| Logistic Regression: GFAP, CRP, VCAM, IL-6 (Gender), sTNFR1 (Gender) | 0.875 | 0.035 | 0.000 | 0.806 0.944 | 0.882 | 0.033 | 0.000 | 0.818 0.946 | 0.914 | 0.041 | 0.000 | 0.835 0.994 |

Figure 9:
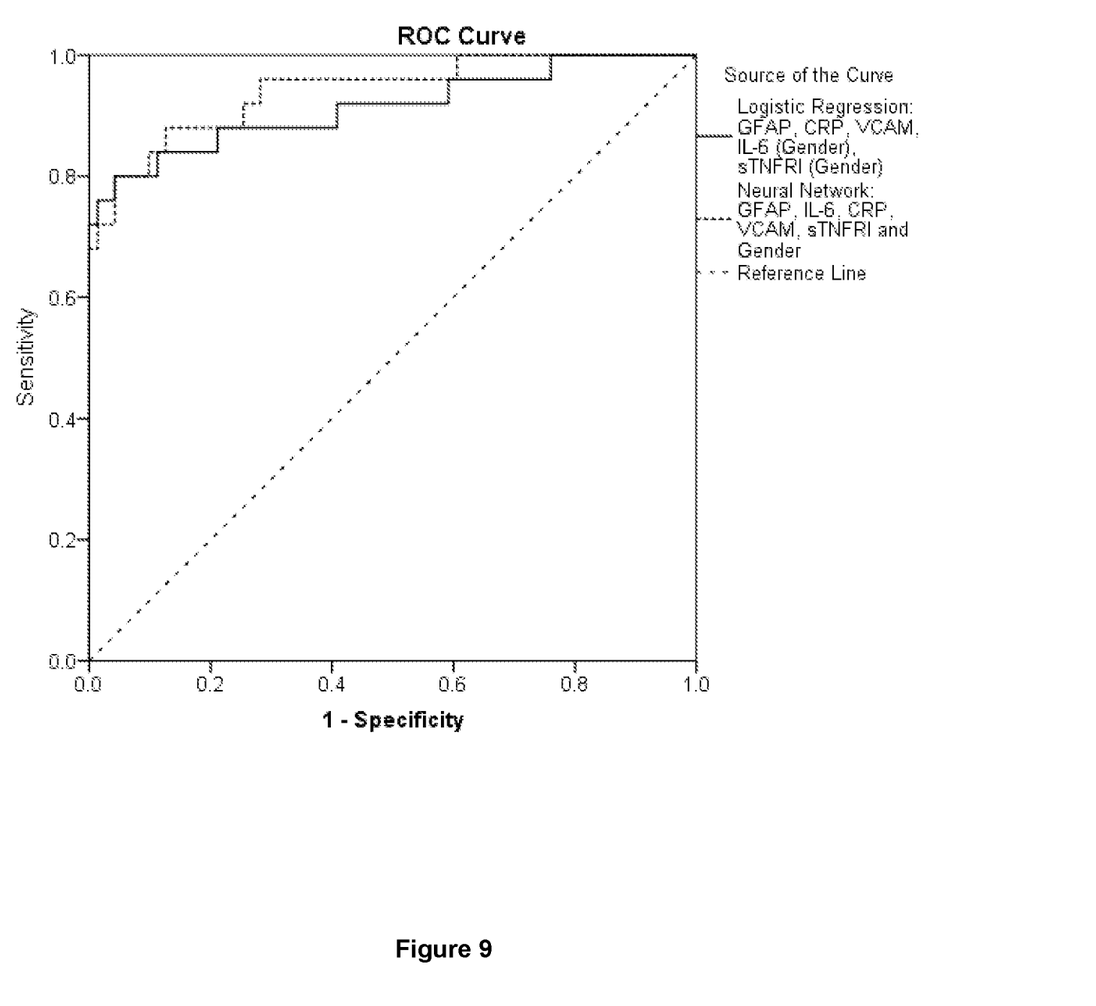
FIG. 9 shows the data and corresponding ROC curve analysis respectively comparing logistic regression and neural network methods for devising a classification algorithm for distinguishing HS from all stroke types.

In addition, alternative approaches to devising categorisation algorithms, such as using artificial neural networks (see FIG. 9 and Table 5), display similar performance characteristics.

TABLE 5

Area Under the Curve

| Test Result Variable(s) | Area | Std. Error[a] | Asymptotic Sig.[b] | Asymptotic 95% Confidence Interval | |
|---|---|---|---|---|---|
| | | | | Lower Bound | Upper Bound |
| Logistic Regression: GFAP, CRP, VCAM, IL-6 (Gender), sTNFRI (Gender) | 0.914 | 0.041 | 0.000 | 0.835 | 0.994 |
| Neural Network: GFAP, IL-6, CRP, VCAM, sTNFRI and Gender | 0.941 | 0.029 | 0.000 | 0.885 | 0.998 |

[a] Under the nonparametric assumption
[b] Null hypothesis: true area = 0.5

This further exemplifies the robust nature in combining the biomarkers of interest in an algorithm derived by any method known in the art.

ABBREVIATIONS

GFAP—glial fibrillary acidic protein
IL-6—interleukin-6
ICAM-1—intracellular adhesion molecule-1
VCAM-1—vascular cell adhesion molecule-1

CRP—C-reactive protein
FABP—fatty acid binding protein
sTNFR1—soluble TNFα receptor 1
L-selectin—lymphocyte cell adhesion molecule (CD62L)
P-selectin—platelet cell adhesion molecule
D-dimer—fibrin degradation product

The invention claimed is:

1. An assay for determining a concentration of biomarkers consisting of VCAM-1, GFAP and CRP in an ex vivo sample obtained from a patient who has suffered or is suffering a stroke and is in need of diagnosis of haemorrhagic stroke, ischemic stroke or transient ischemic attack, comprising
    i) contacting the ex vivo sample with probes specific for VCAM-1, GFAP and CRP, wherein each probe binds specifically to VCAM-1, GFAP or CRP;
    ii) carrying out a quantitative immunoassay to detect the concentration of the biomarkers present in the ex vivo sample and obtain a concentration value, wherein the probes specific for the biomarkers are present on the surface of a substrate;
    iii) inputting the concentration value of each of the biomarkers present in the ex vivo sample of the biomarkers into a statistical algorithm or algorithms to produce an output value that correlates with a differential diagnosis of haemorrhagic stroke, ischemic stroke or transient ischaemic attack; and
    iv) diagnosing haemorrhagic stroke, ischemic stroke or transient ischaemic attack based on the output value from the statistical algorithm or algorithms;
    v) administering appropriate treatment based on the diagnosis of haemorrhagic stroke, wherein the patient is administered treatment in the form of surgery to repair one or more damaged blood vessels.

2. An assay according to claim 1, wherein the statistical algorithm includes a logistic regression equation.

3. An assay according to claim 1, wherein the ex vivo sample is a blood, serum or plasma sample.

4. An assay for determining a concentration of biomarkers consisting of VCAM-1, GFAP and CRP in an ex vivo sample obtained from a patient who has suffered or is suffering a stroke and is in need of diagnosis of haemorrhagic stroke, ischemic stroke or transient ischemic attack, comprising
    i) contacting the ex vivo sample with probes specific for VCAM-1, GFAP and CRP, wherein each probe binds specifically to VCAM-1, GFAP or CRP;
    ii) carrying out a quantitative immunoassay to detect the concentration of the biomarkers present in the ex vivo sample and obtain a concentration value, wherein the probes specific for the biomarkers are present on the surface of a substrate;
    iii) inputting the concentration value of each of the biomarkers present in the ex vivo sample of the biomarkers into a statistical algorithm or algorithms to produce an output value that correlates with a differential diagnosis of haemorrhagic stroke, ischemic stroke or transient ischaemic attack; and
    iv) diagnosing haemorrhagic stroke, ischemic stroke or transient ischaemic attack based on the output value from the statistical algorithm or algorithms
    v) administering appropriate treatment based on the diagnosis of ischemic stroke, wherein the patient is administered a treatment to break-down clots.

5. An assay according to claim 4, wherein the statistical algorithm includes a logistic regression equation.

6. An assay according to claim 4, wherein the ex vivo sample is a blood, serum or plasma sample.

7. An assay according to claim 4, wherein the treatment to break-down clots is thrombolytic therapy.

8. An assay for determining a concentration of biomarkers consisting of VCAM-1, GFAP and CRP in an ex vivo sample obtained from a patient who has suffered or is suffering a stroke and is in need of diagnosis of haemorrhagic stroke, ischemic stroke or transient ischemic attack, comprising
    i) contacting the ex vivo sample with probes specific for VCAM-1, GFAP and CRP, wherein each probe binds specifically to VCAM-1, GFAP or CRP;
    ii) carrying out a quantitative immunoassay to detect the concentration of the biomarkers present in the ex vivo sample and obtain a concentration value, wherein the probes specific for the biomarkers are present on the surface of a substrate;
    iii) inputting the concentration value of each of the biomarkers present in the ex vivo sample of the biomarkers into a statistical algorithm or algorithms to produce an output value that correlates with a differential diagnosis of haemorrhagic stroke, ischemic stroke or transient ischaemic attack; and
    iv) diagnosing haemorrhagic stroke, ischemic stroke or transient ischaemic attack based on the output value from the statistical algorithm or algorithms
    v) administering appropriate treatment based on the diagnosis of transient ischaemic attack, wherein the patient is administered treatment in the form of one or more blood thinners.

9. An assay according to claim 8, wherein the statistical algorithm includes a logistic regression equation.

10. An assay according to claim 8, wherein the ex vivo sample is a blood, serum or plasma sample.

* * * * *